United States Patent [19]

Morris

[11] Patent Number: 4,919,118
[45] Date of Patent: Apr. 24, 1990

[54] MOTION LIMITER FOR SHORT LEG WALKER

[75] Inventor: John C. Morris, Castro Valley, Calif.

[73] Assignee: Orthopedic Technology, Inc., San Leandro, Calif.

[21] Appl. No.: 394,398

[22] Filed: Aug. 14, 1989

[51] Int. Cl.$^5$ .............................................. A61F 5/04
[52] U.S. Cl. .................................... 128/88; 128/83.5; 128/80 H
[58] Field of Search ................ 128/80 R, 80 A, 80 C, 128/80 F, 80 H, 84 R, 84 A, 84 B, 84 C, 83.5, 88, 166; 403/113, 116, 292, 298

[56] References Cited

U.S. PATENT DOCUMENTS

| | | | |
|---|---|---|---|
| 649,237 | 5/1900 | Dyson | 128/88 |
| 2,141,099 | 12/1938 | Walters | 128/83.5 |
| 3,788,307 | 1/1974 | Kistner | 128/77 |
| 4,057,056 | 11/1977 | Payton | 128/83.5 |
| 4,099,525 | 7/1978 | McCarthy | 128/87 R |
| 4,407,276 | 10/1983 | Bledsoe | 128/80 C |
| 4,446,856 | 5/1984 | Jordan | 128/80 R |
| 4,454,871 | 6/1984 | Mann | 128/80 H |
| 4,510,927 | 4/1985 | Peters | 128/80 H |
| 4,517,968 | 5/1985 | Greene | 128/80 H |
| 4,641,639 | 2/1987 | Padilla | 128/83.5 |
| 4,771,768 | 9/1988 | Crispin | 128/88 |
| 4,809,686 | 3/1989 | Crane | 128/80 H |

Primary Examiner—Robert A. Hafer
Assistant Examiner—Lynda M. Cofsky
Attorney, Agent, or Firm—Townsend and Townsend

[57] ABSTRACT

A motion limiter (2) for use with a short leg walker (4) includes a threaded shaft (20) passing freely through a hole (42) in a sliding block or guide (36) that is pivotally attached preferably to an upper part (6) of the walker. The lower end (28) of the shaft is preferably pivotally mounted in a recess (34) in the lower portion (10) of the walker and the remainder of the shaft is free to slide within the hole in the sliding block within a recess (26) in the upper part of the walker. The position of stop members (64, 68), threaded to the shaft above and below the block, determine the amount or fraction of the shaft permitted to pass through the hole in the sliding block. As the stop members are positioned along the shaft relatively far apart from one another, a greater length of the threaded shaft is permitted to pass through the sliding block, thereby increasing the range of motion of the walker. Conversely, as the stop members are moved relatively closer together, the range of motion decreases. If the stop members are positioned so as to abut the sliding block, no range of motion is permitted. The stop members may be positioned by a user without using tools.

21 Claims, 3 Drawing Sheets

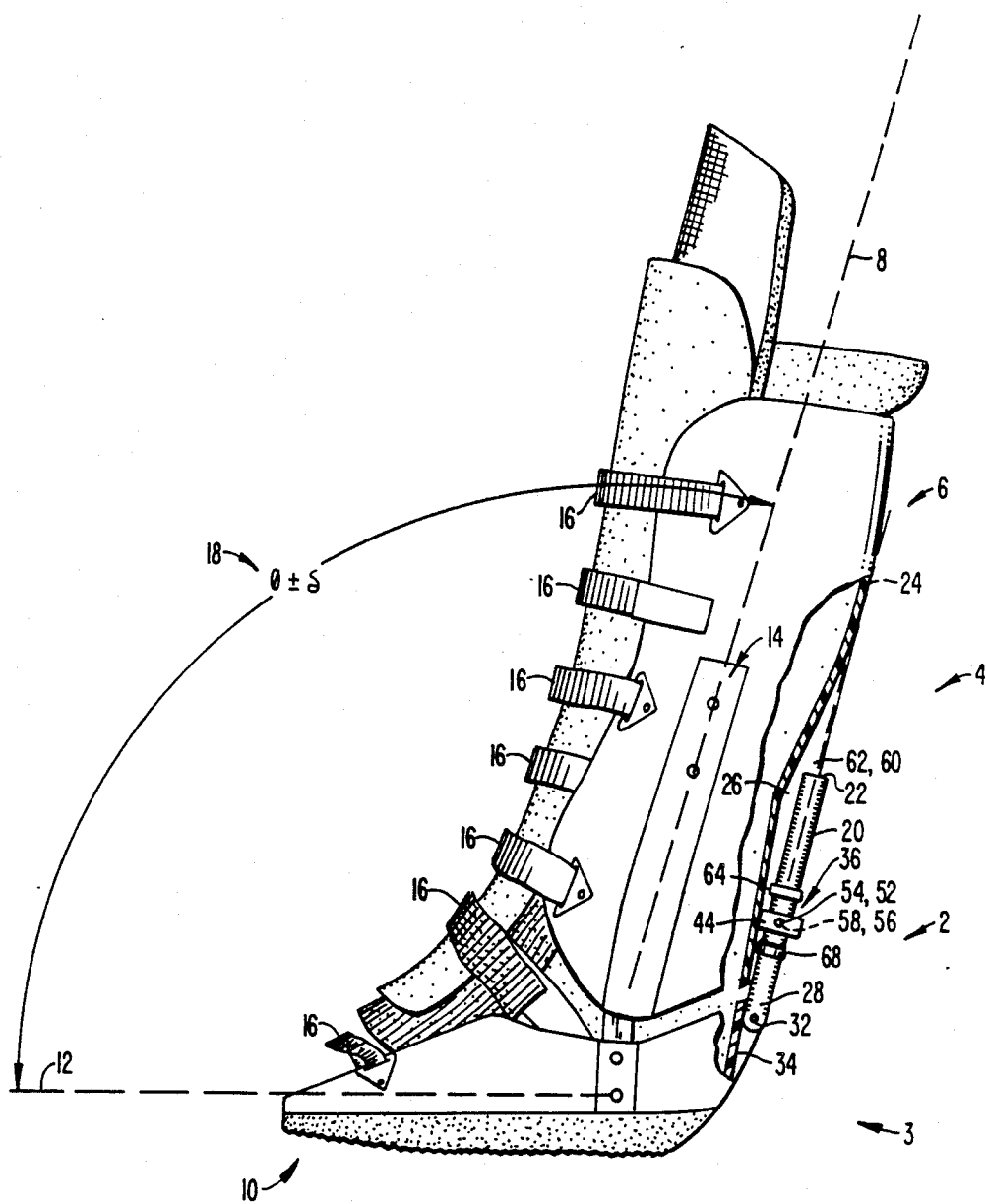
FIG._1.

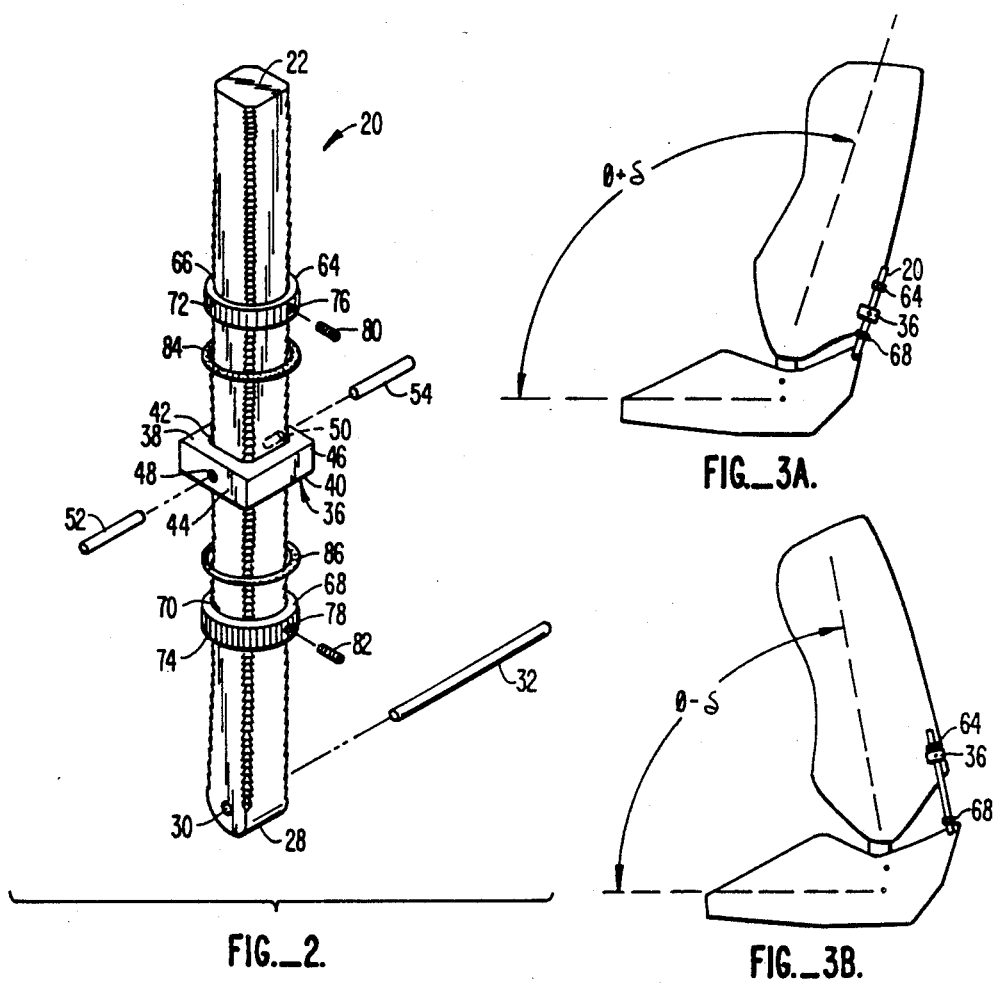
FIG._2.  FIG._3A.  FIG._3B.
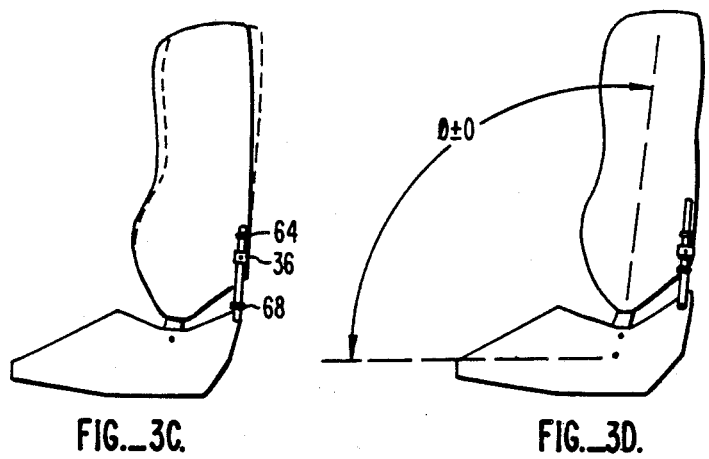
FIG._3C.  FIG._3D.

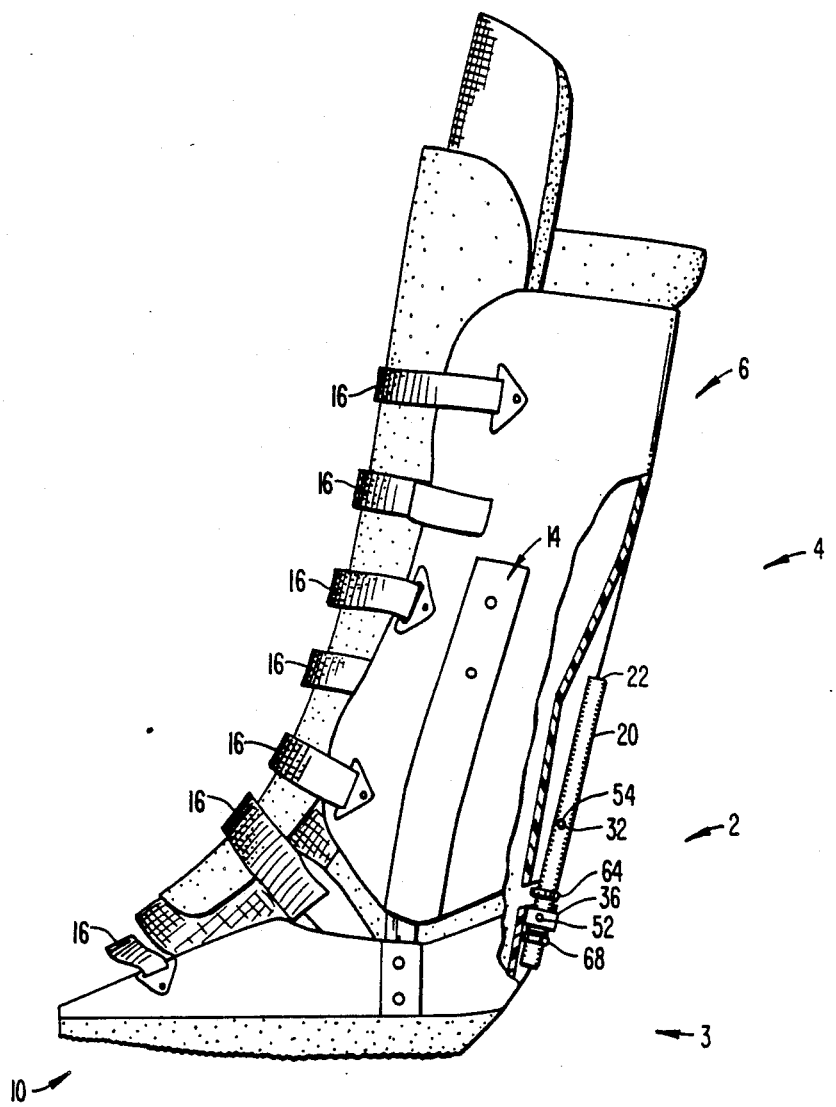
FIG._4.

MOTION LIMITER FOR SHORT LEG WALKER

BACKGROUND OF THE INVENTION

This invention relates generally to motion limiters for orthopedic short leg walker devices for ambulatory patients.

Short leg walkers are orthopedic leg devices worn by ambulatory patients recovering from a leg injury. Limiting the range of molten on short leg walkers is a time consuming chore, often requiring numerous adjustments with a screwdriver or other tool. Further, the apparatus for limiting range of motion is typically cumbersome, and can snag or catch the user's clothing. A short leg walker with a typical prior art motion limiter is disclosed in U.S. Pat. No. 4,771,768 to Crispin wherein a separate limiting mechanism is required on the medial and distal sides of the walker. Since each of Crispin's limiting mechanisms requires screwdriver adjustment of two elements, a total of four adjustments must be made to limit motion in the walker. Further, from a manufacturing standpoint, such motion limiting devices are not universal in the sense that one size device does not readily accommodate different sized walkers.

SUMMARY OF THE INVENTION

The present invention is a range of motion limiter for a short leg walker. Short leg walkers typically have an upper member that surrounds the user's lower leg (below the knee and above the ankle), a lower member that surrounds the user's foot, and hinge mechanisms for joining the upper and lower members to permit relative motion therebetween as the user walks or otherwise moves the ankle joint.

The present invention advantageously limits motion with a simple mechanism that is capable of accomodating varying sizes of short leg walkers. Adjustment of the present invention is straightforward and can be made without tools. Further, the present invention may be located in a recess at the rear of the walker to minimize snagging of the user's clothing.

A physician might permit a user with a newly injured leg to ambulate providing there is no relative motion between the lower leg and the foot. As the leg begins to recover, a gradual increase in range of motion may be permitted. It is the function of the present invention to controllably limit the range of permissible motion between the user's lower leg and foot.

The present invention includes a shaft pivotally joined at one shaft end to, preferably, the lower walker member, and a sliding block pivotally attached to the remaining, preferably upper, walker member. The sliding block has a hole sized to accommodate the shaft which passes freely therethrough. A stop member with a hole sized to engage the shaft is mounted around the shaft above the block, and a similar stop member is mounted around the shaft below the block.

The amount of relative movement between the upper and lower leg members, i.e. the range of motion of the walker, is determined by the position of the stop members along the shaft. The position of the stop members on the shaft are determined by the user or the physician. If the stop members are positioned relatively far apart from each other, a relatively large amount or fraction of the shaft is permitted to slide through the block, and the walker is permitted a greater range of motion. If the stop members are positioned relatively close together, less of the shaft is permitted to slide through the block, and a relatively smaller range of motion results. If the stop members are positioned so as to contact the block without permitting any portion of the shaft to slide therethrough, the walker is permitted no relative motion.

It is preferred that the upper and lower walker members define a recessed channel at the rear of the walker wherein the present invention is disposed. So located, the motion limiter is out of the way, and unlikely to snag a user's clothing. Nonetheless, the user still has ready access to the stop members for purposes of adjusting the range of motion.

Since the range of motion is controlled by positioning the stop members along the length of the threaded shaft, the present invention is universal in the sense that one size motion limiter may be used with walkers of various sizes. Finally, the present invention allows the range of motion to be readily adjusted without the use of tools in that the position of the stop members may be adjusted with the user's fingers.

BRIEF DESCRIPTION OF THE DRAWINGS

FIG. 1 shows in perspective a short leg walker including a motion limiter according to the present invention;

FIG. 2 is a partial exploded view of the motion limiter shown in FIG. 1.

FIGS. 3A–3D schematically represent various range of motion adjustments available according to the present invention.

FIG. 4 shows an alternative embodiment of the present invention.

DETAILED DESCRIPTION OF THE PREFERRED EMBODIMENT

FIG. 1 shows a motion limiter 2 located at the rear portion 3 of a short leg walker 4. Short leg walker 4 includes an upper walker member 6 defining an upper major upper axis 8, a lower walker member 10 defining a lower major axis 12, and a pair of hinge mechanisms 14 located on either side of the walker 4 joining members 6 and 10. In use, the upper member 6 is attached to a user's lower leg and the lower member 10 is attached to the user's foot, the attachment typically being with straps 16. Such walkers are known in the art, and for that reason will not be described in further detail.

Axes 8 and 12 define between them an angle 18 ($\phi \pm \delta$) through which upper member 6 and lower member 10 are capable of motion relative to one another as the user's leg is flexed, as during walking. It is the function of the present invention 2 to controllably define the range of motion 18 ($\phi \pm \delta$). If desired, the present invention is capable of locking walker 4 into a fixed position, wherein the range of motion is zero, i.e., $\delta = 0$.

With reference to FIGS. 1 and 2, the present invention includes a threaded shaft 20 whose upper end 22 is capable of movement along a moveable shaft axis 24 that is more or less parallel to axis 8. Such movement occurs preferably within a recess 26 formed in the upper member 6. Shaft 20 has a lower end 28 with a hole 30 therethrough for receiving a retaining pin 32 for pivotally mounting the lower end 28 in a lower recess 34 formed in lower member 10. Recesses 26 and 34 and are simply concavities formed in the rear section 3 of walker 4 to accommodate the present invention. Thus, the lower end 28 of shaft 20 is pivotally retained within recess 34, while the remainder of shaft 20 is slideably retained within recess 26 by a sliding block 36 that is pivotally mounted within recess 26.

Sliding block or guide 36 has upper and lower surfaces 38, 40, a hole 42 passing therethrough sized to freely accommodate the cross section of the threaded shaft 20, and spaced apart sides 44, 46. Preferably the shape of the hole 42 in block 36 is the same as the cross section of shaft 20. Sides 44, 46 each have a recess 48, 50 for receiving, respectively, pivot pins 52, 54 for pivotally attaching block 36 within recess 26 in upper member 6. Preferably pivot pins 52, 54 are frictionally retained within holes 56, 58 in the walker sidewalls 60, 62 forming recess 26. Block 36 could of course by pivotally attached to upper member 6 using, for example, screws, loosely fitting rivets or the like. Thus, shaft 20 is free to slide within the hole 46 in block 36 as the upper and lower members 6, 10 of the walker 4 move relative to one another. As shaft 20 moves, the inclination of the variable shaft axis 24 relative to the major axis 8 is free to change. Axis 24 is defined at one end by retaining pin 32, and is defined at the other end by hole 42 in block 36. Sliding block 36 is preferably made of a low friction material such as nylon or brass, whereas shaft 20 is preferably made of metal to provide strength and durability. Other materials such as plastics could be used however.

A first stop member 64 having a threaded opening 66 sized to threadably engage shaft 20 is threadably attached to shaft 20 between upper surface 28 of block 36 and the upper end 20 of shaft 20. A similar second stop member 68 having a threaded opening 70 is threadably attached to shaft 20 between the lower surface 40 of block 36 and the lower end of shaft 20. Preferably each stop member 64, 68 includes a knurled outer circumference 72, 74 as shown in FIG. 2 to facilitate adjustment of the range of motion by rotating member 64 and/or 68 along shaft 20 with a user's fingers. Further, members 64, 68 preferably include radially extending threaded holes 76, 78 for receiving set screws 80, 82 for locking the stop member in a desired position along the length of threaded shaft 20.

Optionally, the present invention includes resilient washers 80, 82 disposed between the stop members 64, 68 and the sliding block 36, to provide a shock absorbing function as the walker 4 approaches the limit of the allowable range of motion.

Shaft 20 preferably defines a square cross section as shown in FIG. 2. Such a cross section allows the radially inward ends of the set screws 80, 82 to abut a flat side of shaft 20 when locking stop members 64, 68 in a user chosen position. Further, a square cross section eliminates protuberances between shaft 20 and block 36 at the point of contact with the result that block 36 will slide relatively noiselessly along shaft 20, in use. Shaft 20 could, however, have a cross section with any number of flat sides such as 5, 6, 7, etc., or a round cross section. While a round cross section affords an infinite number of sides against which set screws 80, 82 can abut, and thus finer range of motion resolution, a flat cross section affords a firmer locking surface, i.e., a flat side as opposed to a curved surface. For example, if shaft 20 has a square cross section, and the desired locking position for one of the stop members 64, 68 causes the set screw 80, 82 to fall on a 90° corner of shaft 20, it might be necessary to rotate the stop member a few degrees in one direction or the other to allow the set screw to contact a flat side of the cross section. However such slight rotation of the stop member would somewhat affect the desired range of motion for the walker.

The pitch of the threads on shaft 20 and stop members 64, 68 also affect the range of motion resolution. In the preferred embodiment a pitch of about 24 threads/inch is used, although other pitches could be used as well. Alternatively, shaft 20 and stop members 64, 68 could have no threads (i.e., an infinite thread pitch) and the stop members 64, 68 could be positioned at an infinite number of locations along shaft 20 and locked into place with set screws 80, 82.

In practice, the user mounts walker 4 to his or her leg in the usual manner. Range of motion is then limited by adjusting the position of the first and/or second stop member 64, 68 with the user's fingers until the desired range of motion is set. Once set, stop members 64, 68 may be locked in position with set screws 80, 82. As an alternative to set screws 80, 82, each stop member 64, 68 could be replaced by two stop members, neither of which has a set screw. The inner most stop members (i.e., those closest to the sliding block 36) would be adjusted with a user's fingers to define the range of motion, and the remaining stop members would then be rotated with the user's fingers to abut the inner most stop members, thereby fixing them in the chosen position along shaft 20. Stop members 64, 68 could be of a self-locking type as well.

As shown in FIGS. 3A and 3B, when stop members 64, 68 are positioned relatively far apart from one another along shaft 20, a larger range of motion is permitted because the amount or fraction of the shaft 20 permitted to slide through block 36 is relatively large. As shown in FIG. 3C, when stop members 64, 68 are positioned closer to one another along shaft 20, the fractional amount of shaft 36 permitted to pass through block 36 is relatively small, and a smaller range of motion is permitted. Finally, as shown by FIG. 3D, when stop members 64, 68 are positioned substantially adjacent to sliding block 36, the fraction of shaft 36 permitted to slide through block 36 is zero, and the leg walker 4 will be essentially locked at a fixed angle $\phi$ with the allowable range $\delta=0$. Depending upon the relative position of the stop members 64, 68, i.e., positioned together relatively near the upper end 20 or the lower end 28 of shaft 20, a relative range of motion $\pm\delta$ can be achieved over various angles $\phi$.

FIG. 4 shows an alternative embodiment wherein sliding block 36 is pivotally mounted in a recess 34 in lower walker member 10, and upper end 22 of shaft 20 is pivotally mounted within a recess 26 in upper walker member 6. The operation of this alternative embodiment remains substantially the same as that of FIG. 1.

Modifications and variations may be made to the disclosed embodiments without departing from the subject of the invention as defined by the following claims. Those skilled in the art will appreciate that stop member 68 may be omitted and lower retaining pin 32 used as a fixed stopping member. Such a configuration would not, however, permit the flexibility in adjustment of range of motion provided by the preferred embodiment described herein. Alternatively, stop members 64, 68 could be spring-load devices that are clipped on to shaft 20 at user determined locations.

What is claimed is:

1. A motion limiter for a short leg walker of the type having an upper member joined to a lower member to permit relative movement therebetween, the motion limiter comprising:

a shaft having a first end, a second end, a length therebetween and defining a cross section, the second shaft end adapted to be pivotally attached to a chosen one of the upper and lower members;

a guide having upper and lower surfaces and defining a hole therethrough sized to accommodate the cross section of said shaft, the guide adapted to be pivotally attached to the unchosen one of the upper and lower members;

said shaft being disposed within said hole whereby a sliding movement of the shaft through said guide is permitted as the first and second members move relative to one another; and first and second stop members positioned along the shaft on either side of the guide to limit the movement of the shaft through the guide thereby limiting the range of motion of the upper member relative to the lower member, at least said first stop member being adjustably positionable along the shaft to adjust said range of motion.

2. The limiter of claim 1, wherein said first stop member includes an opening formed therein sized to accommodate the cross section of said shaft;

said shaft being disposed within the opening in said first stop member; and further including means for fixing the first stop member in a user determined position along the length of the shaft.

3. The limiter of claim 2, wherein the shaft and the opening in the first stop member include threads for threadable engagement with each another;

rotation of the first stop member causing a position change of the first stop member along the length of the shaft, thereby limiting the range of motion.

4. The limiter of claim 1, wherein the cross section of the shaft has a flat side.

5. A motion limiter for a short leg walker of the type having an upper member joined to a lower member to permit relative movement therebetween, the motion limiter comprising:

a threaded shaft having an upper end, a lower end, a length therebetween and defining a cross section, the lower shaft end adapted to be pivotally attached to the lower member;

a guide having upper and lower surfaces and defining a hole therethrough sized to accommodate the cross section of said shaft, the guide adapted to be pivotally attached to the upper member;

said shaft being disposed within said hole whereby a sliding movement of the shaft through said guide is permitted as the first and second members move relative to one another; and a first stop member defining a threaded opening sized to threadably engage said shaft, the first stop member being threadably attached to said shaft between the upper surface of said guide and the upper end of said shaft;

the position of said first stop member on said shaft determining an upper portion of the shaft length permitted to slide through said hole in said guide so as to limit a range of motion of the upper member relative to the lower member.

6. The motion limiter of claim 5, further including a second stop member defining a threaded opening sized to threadably engage said shaft, the second stop member being threadably attached to said shaft between the lower surface of said guide and the lower end of the shaft;

the position of said second stop member on said shaft determining a lower portion of the shaft length permitted to slide through said hole in said guide so as to limit a range of motion of the upper member relative to the lower member.

7. The motion limiter of claim 5, wherein the cross section of the shaft has a flat side.

8. A motion limiter for a short leg walker of the type having an upper member joined to a lower member to permit relative movement therebetween, the motion limiter comprising:

a shaft having a first end, a second end, a length therebetween and defining a cross section, and adapted to be pivotally attached at the second shaft end to a chosen one of the upper and lower members;

a guide having upper and lower surfaces and defining a hole therethrough sized to accommodate the cross section of said shaft, the guide being adapted to be pivotally attached to the unchosen one of the upper and lower members;

said shaft being disposed within said hole whereby a sliding movement of the shaft through said guide is permitted as the first and second members move relative to one another; and means for limiting a portion of the shaft length permitted to slide through said hole in said guide as the first and second walker members move relative to one another, so as to correspondingly limit a range of motion of the walker determined by the portion of the shaft length permitted to slide through said hole in said guide.

9. The limiter of claim 1, wherein said means for limiting includes:

a stop member defining an opening sized to accommodate the cross section of said shaft, the shaft being disposed within said opening; and means for fixing the stop member in a user determined position along the length of the shaft between an end of the shaft and a surface of the guide.

10. A short leg walker with an adjustable limit of range of motion, comprising:

an upper member sized to receive a user's lower leg:

a lower member sized to receive a user's foot;

means for joining the lower member to the upper member to permit relative movement therebetween;

a shaft having a first end, a second end, a length therebetween and defining a cross section, the second shaft end being pivotally attached to a chosen one of the upper and lower members;

a guide having upper and lower surfaces and defining a hole therethrough sized to accommodate the cross section of said shaft, the guide being pivotally attached to the unchosen one of the upper and lower members;

said shaft being disposed within said hole to permit sliding movement of the shaft through said guide as the first and second members move relative to one another;

first and second stop members positioned along the shaft on either side of the guide to limit the movement of the shaft through the guide thereby limiting the range of motion of the upper member relative to the lower member, at least said first stop member being adjustably positionable along the shaft to adjust said range of motion.

11. The walker of claim 10, wherein said first stop member includes an opening formed therein sized to accommodate the cross section of said shaft;

said shaft being disposed within the opening in said first stop member; and further including means for fixing the first stop member in a user determined position along the length of the shaft.

12. The walker of claim 11, wherein the shaft and the opening in the first stop member include threads for threadable engagement with one another;

rotation of the first stop member causing a position change of the first stop member along the length of the shaft, thereby limiting the range of motion.

13. The walker of claim 10, wherein the cross section of the shaft has a flat side.

14. The walker of claim 10, wherein the upper and lower member each define a recess at a rear of the walker, said recesses sized to receive the shaft, guide and first and second stop members.

15. A short leg walker with an adjustable limit of range of motion, comprising:

an upper member sized to receive a user's lower leg;

a lower member sized to receive a user's foot;

means for joining the lower member to the upper member to permit relative movement therebetween;

a threaded shaft having an upper end, a lower end, a length therebetween and defining a cross section, the lower shaft end being pivotally attached to the lower member;

a guide having upper and lower surfaces and defining a hole therethrough sized to accommodate the cross section of said shaft, the guide being pivotally attached to the upper member;

said shaft being disposed within said hole to permit sliding movement of the shaft through said guide as the first and second members move relative to one another; and a first stop member defining a threaded opening sized to threadably engage said shaft, the first stop member being threadably attached to said shaft between the upper surface of said guide and the upper end of said shaft;

the position of said first stop member on said shaft determining a fraction of an upper shaft length permitted to slide through said hole in said guide so as to limit a range of motion of said walker.

16. The walker of claim 15, further including a second stop member defining a threaded opening sized to threadably engage said shaft, the second stop member being threadably attached to said shaft between the lower surface of said guide and the lower end of said shaft;

the position of said second stop member on said shaft determining a lower portion of the shaft length permitted to slide through said hole in said guide so as to limit a range of motion of the upper member relative to the lower member.

17. The walker of claim 15, wherein the cross section of the shaft has a flat side.

18. The walker of claim 15, wherein the upper and lower member each define a recess at a rear of the walker, said recesses sized to receive the shaft, guide and first and second stop members.

19. A method for limiting motion in a short leg walker of the type having an upper member joined to a lower member to permit relative movement therebetween, the method comprising:

pivotally attaching a shaft at a lower shaft end to the lower member of the walker;

pivotally attaching a guide to the upper member of the walker, the guide defining a through hole sized to allow said shaft to slide therethrough;

disposing said shaft such that an upper portion thereof slides through said hole in said guide as the upper and lower members of the walker are moved relative to one another;

limiting an amount of the shaft permitted to slide through said hole as the upper and lower members of the walker are moved relative to one another, so as to limit a range of motion of the walker.

20. The method of claim 19, wherein said shaft and guide are disposed at a rear of the walker.

21. The method of claim 19, wherein said shaft and guide are disposed within a cavity in a rear portion of the walker.

* * * * *